(12) United States Patent
Skraly

(10) Patent No.: US 8,071,355 B2
(45) Date of Patent: Dec. 6, 2011

(54) POLYHYDROXYALKANOATE PRODUCTION BY COENZYME A-DEPENDENT ALDEHYDE DEHYDROGENASE PATHWAYS

(75) Inventor: Frank A. Skraly, Somerville, MA (US)

(73) Assignee: Metabolix, Inc., Cambridge, MA (US)

( * ) Notice: Subject to any disclaimer, the term of this patent is extended or adjusted under 35 U.S.C. 154(b) by 1847 days.

(21) Appl. No.: 10/661,939

(22) Filed: Sep. 12, 2003

(65) Prior Publication Data

US 2004/0106176 A1 Jun. 3, 2004

Related U.S. Application Data

(60) Provisional application No. 60/410,087, filed on Sep. 12, 2002.

(51) Int. Cl.
*C12N 1/20* (2006.01)
*C12N 1/16* (2006.01)
*C12N 15/00* (2006.01)
*C12N 9/16* (2006.01)
*C12P 7/42* (2006.01)
*C12P 7/62* (2006.01)
*C07H 21/04* (2006.01)

(52) U.S. Cl. ............... 435/252.3; 435/254.2; 435/320.1; 435/146; 435/135; 435/196; 536/23.2

(58) Field of Classification Search ............... 435/252.3, 435/320.1, 146; 536/23.2
See application file for complete search history.

(56) References Cited

U.S. PATENT DOCUMENTS

| | | | |
|---|---|---|---|
| 4,477,654 A | 10/1984 | Holmes et al. |
| 4,910,145 A | 3/1990 | Holmes et al. |
| 5,245,023 A | 9/1993 | Peoples et al. |
| 5,250,430 A | 10/1993 | Peoples et al. |
| 5,480,794 A | 1/1996 | Peoples et al. |
| 5,489,470 A | 2/1996 | Noda |
| 5,502,116 A | 3/1996 | Noda |
| 5,512,669 A | 4/1996 | Peoples et al. |
| 5,534,432 A | 7/1996 | Peoples et al. |
| 5,563,239 A | 10/1996 | Hubbs et al. |
| 6,329,183 B1 | 12/2001 | Skraly et al. |
| 6,689,589 B2 | 2/2004 | Huisman et al. |

FOREIGN PATENT DOCUMENTS

| | | |
|---|---|---|
| WO | WO 98/39453 | 9/1998 |
| WO | WO 99/14313 | 3/1999 |
| WO | WO 00/43523 | 7/2000 |
| WO | WO 02/08428 | 1/2002 |

OTHER PUBLICATIONS

Goodlove et al. Cloning and sequence analysis of the fermentative alcohol-dehydrogenase-encoding gene of *Escherichia coli*, Gene Dec. 21, 1989;85(1):209-14.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Branden et al. Introduction to protein structure, Gerald Publishing Inc., New York, p. 247, 1991.*
Whisstock et al. Quaterly Reviews of Biophysics, 2003, "Prediction of protein function from protein sequence and structure", 36(3): 307-340.*
Seffernick et al. Melamine deaminase and atrazine chlorohydrolase: 98 percent identical but functionally different, J Bacteriol. Apr. 2001;183(8):2405-10.*
Agostini, et al., "Synthesis and Characterization of Poly-β-Hydroxybutyrate. I. Synthesis of Crystalline DL Poly-β-Hydroxybutyrate from DL-β-Butyrolactone," *Polym. Sci.* Part A-1 9:2775-87 (1971).
Braunegg, et al., "Polyhydroxyalkanoates, biopolyesters from renewable resources: physiological and engineering aspects," *J. Biotech*. 65: 127-161 (1998).
Bruhn & Müller, "Preparation and characterization of spray-dried poly(DL-lactide) Micro Spheres," *Proceed. Intem. Symp. Control. Rel. Bioact. Mater*. 18:668-69 (1991).
Byrom, "Miscellaneous Biomaterials" in Biomaterials (D. Byrom, ed.) pp. 333-359 (MacMillan Publishers, London 1991).
Choi & Lee, "Factors affecting the economics of polyhydroxyalkanoate production by bacterial fermentation," *Appl. Microbiol. Biotechnol*. 51:13-21 (1999).
Clark & Rod, "Regulatory mutations that allow the growth of *Escherichia coli* on butanol as carbon source," *J. Mol. Evol*. 25: 151-158 (1987).
Conti, et al., "Use of polylactic acid for the preparation of microparticulate drug delivery systems," *J. Microencapsulation* 9: 153-166 (1992).
Daniel, et al., "Purification of 1,3-propanediol dehydrogenase from *Citrobacter freundii* and cloning, sequencing, and overexpression of the corresponding gene in *Escherichia coli*," *J. Bacteriol*. 177(8): 2151-2156 (1995). Doi, "Microbial synthesis, physical properties, and bioegradability of polyhydroxyalkanoates," *Macromol. Symp*. 98: 585-599 (1995).
Dubois, et al., "Macromolecular engineering of polylactones and polylactides. 12. Study of the depolymerization reactions of pol(ε-caprolactone) with functional aluminum alkoxide end groups," *Macromolecules* 26:4407-4412 (1993).
Fukui, et al., "Biosynthesis of poly(3-hydroxybutyrate-co-3 hydroxyvalerate-co-3hydroxy-heptanoate) tertpolymers by recombinant *Alcaligenes eutrophus*," *Biotechnol. Lett*. 19: 1093-1097 (1997).
Gerngross & Martin, "Enzyme-catalyzed synthesis of poly[(R)-(–)-3-hydroxybutyrate]: formation of macroscopic granules in vitro," *Proc. Natl. Acad. Sci*. USA 92:6279-83 (1995).

(Continued)

*Primary Examiner* — Robert Mondesi
*Assistant Examiner* — Iqbal H Chowdhury
(74) *Attorney, Agent, or Firm* — Pabst Patent Group LLP

(57) ABSTRACT

Organisms are provided containing genes encoding one or more enzymes, Coenzyme-A-dependent aldehyde dehydrogenase, acyl-CoA transferase, acyl-CoA synthetase, β-ketothiolase, acetoacetyl-CoA reductase and/or PHA synthase. In some cases one or more of these genes are native to the host organism and the remainder are heterologous genes provided by genetic engineering. These organisms produce poly (3-hydroxyalkanoate) homopolymers or co-polymers comprising 3-hydroxalkanoate monomers other than 3-hydroxybutryrate wherein these 3-hydroxyalkanoate units are derived from the enzyme-catalyzed conversion of alcohols to 3-hydroxyacyl-CoA monomers, where at least one step in the conversion pathway involves a Co-enzyme A-dependent aldehyde dehydrogenase activity. The PHA polymers are readily recovered and industrially useful as polymers for articles such as films, latexes, coatings, adhesives, fibers, binders, resins, and medical devices.

8 Claims, 2 Drawing Sheets

OTHER PUBLICATIONS

Gross, et al., "Polymerization of β-monosubstituted-β-propiolactones using trialkylaluminum-water catalytic systems and polymer characterization," *Macromolecules* 21:2657-68 (1988).

Herrero, et al., "Transposon vectors containing non-antibiotic resistance selection markers for cloning and stable chromosomal insertion of foreign genes in gram-negative bacteria," *J. Bacteriol.* 172(11): 6557-6567 (1990).

Hocking & Marchessault, "Syndiotactic poly[(R,S)-β-hydroxybutyrate] isolated from methyaluminoxane-catalyzed polymerization," *Polym. Bull.* 30:163-70 (1993).

Hocking & Marchessault, "Biopolyesters" in *Chemistry and Technology of Biodegradable Polymers*, (G.J.L. Griffin, ed.), pp. 48-96, Chapman and Hall: London, 1994.

Holmes, "Biologically Produced (R)-3-Hydroxyalkanoate Polymers and Copolymers," in *Developments in Crystalline Polymers* (Bassett, ed.) Elsevier: London, pp. 1-65 (1988).

Hori, et al., "Ring-opening copolymerization of optically active β-butyrolactone with several lactones catalyzed by distannoxane complexes: synthesis of new biodegradable polyesters," *Macromolecules* 26:4388-90 (1993).

Hori, et al., "Ring-opening polymerization of optically active β-butyrolactone using distannoxane catalysts: synthesis of high molecular weight poly(3-hydroxybutyrate)," *Macromolecules* 26:5533-34 (1993).

Jenkins & Nunn, "Regulation of the *ato* operon by the *atoC* gene in *Escherichia coli*," *J. Bacteriol.* 169(5): 2096-2102 (1987).

Jenkins & Nunn, "Genetic and molecular characterization of the genes involved in short-chain fatty acid degradation in *Escherichia coli*: the *ato* system," *J. Bacteriol.* 169: 42-52 (1987).

Jesudason & Marchessualt, "Synthetic poly[(R,S)-β-hydroxyalkanoates] with butyl and hexyl side chains," *Macromolecules* 27: 2595-2602 (1994).

Johnson & Lin, "*Klebsiella pneumoniae* 1,3-propanediol: NAD+ oxidoreductase," *J. Bacteriol.* 169(5): 2050-2054 (1987).

Jones & Turner, "Interrelationships between the enzymes of ethanolamine metabolism in *Escherichia coli*," *J. Gen. Microbial* 130(Pt 2): 299-308 (1984).

Jones & Turner, "A model for the common control of enzymes of ethanolamine catabolism in *Escherichia coli*," *J. Gen. Microbiol.* 130(Pt 4): 849-860 (1984).

Kemnitzer, et al., "Preparation of predominantly syndiotactic poly(β-hydroxybutyrate) by the tributylin methoxide catalyzed ring-opening polymerization of racemic β-butyrolactone," *Macromolecules* 26:1221-29 (1993).

Koosha, "Preparation and characterization of biodegradable polymeric drug carriers," Ph.D. Dissertation, 1989, Univ. Nottingham, UK., *Diss. Abstr. Int. B* 51:1206 (1990).

Lafferty, et al., "Microbial Production of Poly-b-hydroxybutyric acid" in *Biotechnology* (H.J. Rehm and G. Reed, eds.), Verlagsgesellschaft, Weinheim, vol. 66, pp. 135-176 (1988).

Le Borgne & Spassky, "Stereoelective polymerization of β-butyrolactone," *Polymer* 30:2312-19 (1989).

Luzier, "Materials derived from biomass/biodegradable materials," *Proc. Natl. Acad. Sci.* USA 89: 839-842 (1992).

Madison & Huisman, "Metabolic engineering of poly(3-hydroxyalkanoates): from DNA to plastic," *Microbiol. Mol. Biol. Rev.* 63(1): 21-53 (1999).

Mathiowitz & Langer, "Polyanhydride microspheres as drug delivery systems" in *Microcapsules Nanopart. Med. Pharm.* (Donbrow, ed.) CRC Press: Boca Raton, Florida, pp. 99-123 (1992).

Maysinger, et al., "Microencapsulation and the grafting of genetically transformed cells as therapeutic strategies to rescue degenerating neurons of the CNS,"*Rev. Neurosci.*, 6:15-33 (1995).

McMillin, et al., "Elastomers for biomedical applications," *Rubber Chemistry and Technology* 67:417-446 (1994).

Muller & Seebach., "Poly(hydroxyalkanoates): a fifth class of physiologically important organic biopolymers," *Angew. Chem. Int. Ed. Engl.* 32: 477-502 (1993).

Ogawa, et al., "A new technique to efficiently entrap leuprolide acetate into microcapsules of poly lactic acid or copoly(lactic/glycolic) acid," *Chem. Pharm. Bull.* 36:1095-103 (1988).

Poznanskaya & Korsova, "Some physicochemical parameters of reactions catalyzed bu glycerol dehydratase," *Biokhimiya* 48: 539-543 (1983).

Saito, et al., "Microbial synthesis and properties of poly(3-hydroxybutyrate-co-4-hydroxybutyrate)," *Polym. Int.* 39: 169 (1996).

Skraly, et al., "Construction and characterization of a 1,3-propanediol operon," *Appl. Environ. Microbiol.* 64: 98-105 (1998).

Slater, et al., "Production of poly-(3-hydroxybutyrate-co-3-hydroxyvalerate) in a recombinant *Escherichia coli* strain," *Appl. Environ. Microbial.* 58: 1089-1094 (1992).

Steinbuchel & Valentin, "Diversity of bacterial polyhydroxyalkanoic acids," *FEMS Microbiol. Lett.* 128:219-28 (1995).

Steinbüchel & Wiese, "*A Pseudomonas* strain accumulating polyesters of 3-hydroxybutyric acid and medium-chain-length 3-hydroxyalkanoic acids," *Appl. Microbiol. Biotechnol.* 37:691-97 (1992).

Steinbüchel, "Polyhydroxyalkanoic Acids" in *Biomaterials* (Byrom, ed.) MacMillan Publishers: London, pp. 123-213 (1991).

Tanahashi & Doi, "Thermal properties and stereoregularity of poly(3-hydroxybutyrate) prepared from optically active β-butyrolactone with a zinc-based catalyst," *Macromolecules* 24:5732-33 (1991).

Tobimatsu, et al., "Cloninng, sequencing, and high level expression of the genes encoding adenosylcobalamin-dependent glycerol dehydrase of *Klebsiella pneumoniae*," *J. Biol. Chem.* 271: 22352-22357 (1996).

Toth, et al., "The *ald* gene, encoding a coenzyme A-acylating aldehyde dehydrogenase, distinguishes *Clostridium beijerinckii* and two other solvent-producing clostridia from *Clostridium acetobutylicum*," *Appl. Environ. Microbiol.* 65(11): 4973-80 (1999).

Valentin, et al., "Identification of 4-hydroxyhexanoic acid as a new constituent of biosynthetic polyhydroxyalkanoic acids from bacteria," *Appl. Microbiol. Biotechnol.* 40:710-16 (1994).

Valentin, et al., "Identification of 4-hydroxyvaleric acid as a constituent of biosynthetic polyhydroxyalkanoic acids from bacteria," *Appl. Microbiol. Biotechnol.* 36: 507-514 (1992).

Williams & Peoples, "Biodegradable plastics from plants," *CHEMTECH* 26:38-44 (1996).

Williams & Peoples, "Making plastics green," *Chem. Br.* 33:29-32 (1997).

Xie, et al., "Ring-opening polymerization of β-bulyrolactone by thermophilic lipases,"*Macromolecules* 30:6997-98 (1997).

Zhang, et al., "Production of polyhydroxyalkanoates in sucrose-utilizing recombinant *Escherichia coli* and *Klebsiella* strains," *Appl. Environ. Microbiol.* 60: 1198-1205 (1994).

Aldor, et al., "Metabolic engineering of a novel propionate-independent pathway for the production of poly(3-hydroxybutyrate-co-3-hydroxyvalerate) in recombinant Salmonella enterica serovar typhimurium", *Appl Environ Microbiol.*, 68(8):3848-54 (2002).

Clark, et al., Acetaldehyde coenzyme A dehydrogenase of *E. coli.*, *J. Bacteriol.*, 144(1):179-84 (1980).

Clark, "The fermentation pathways of *Escherichia coli*", *FEMS Microbiol Rev.*, 5(3):223-34 (1989).

\* cited by examiner

SEQUENCE LISTING

<160> NUMBER OF SEQ ID NOS: 4

<210> SEQ ID NO 1
<211> LENGTH: 48
<212> TYPE: DNA
<213> ORGANISM: Artificial Sequence
<220> FEATURE:
<223> OTHER INFORMATION: Primer

<400> SEQUENCE: 1
ggtggtacct taagaggagg tttttatgaa tcaacaggat attgaaca         48

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
ggtgcggccg cttaaacaat gcgaaacgca tcg         33

<210> SEQ ID NO 3
<211> LENGTH: 48
<212> TYPE: DNA
<213> ORGANISM: Artificial Sequence
<220> FEATURE:
<223> OTHER INFORMATION: Primer

<400> SEQUENCE: 3
ggtcctaggt taagaggagg tttttatgaa tagttcgaca aagatcgc         48

<210> SEQ ID NO 4
<211> LENGTH: 32
<212> TYPE: DNA
<213> ORGANISM: Artificial Sequence
<220> FEATURE:
<223> OTHER INFORMATION: Primer

```
<400> SEQUENCE: 4
ggtactagtc taagcacttg tctcctgttt ac                                    32
```

POLYHYDROXYALKANOATE PRODUCTION BY COENZYME A-DEPENDENT ALDEHYDE DEHYDROGENASE PATHWAYS

CROSS REFERENCE TO RELATED APPLICATIONS

Priority is claimed to U.S. Provisional Application Ser. No. 60/410,087 filed on Sep. 16, 2002.

BACKGROUND OF THE INVENTION

The present invention is generally in the field of methods for making 2-hydroxyacid monomers, and the resulting polyhydroxyalkanoate polymers.

Numerous microorganisms have the ability to accumulate intracellular reserves of PHA polymers. Poly [(R)-3-hydroxyalkanoates] (PHAs) are biodegradable thermoplastic materials, produced from renewable resources, with a broad range of industrial and biomedical applications (Williams and Peoples, 1996, CHEMTECH 26, 38-44). Around 100 different monomers have been incorporated into PHA polymers, as reported in the literature (Steinbüchel and Valentin, 1995, FEMS Microbiol. Lett. 128; 219-228) and the biology and genetics of their metabolism has recently been reviewed (Huisman and Madison, 1998, Microbiology and Molecular Biology Reviews, 63: 21-53).

To date, PHAs have seen limited commercial availability, with only the copolymer poly(3-hydroxybutyrate-co-3-hydroxyvalerate) (PHBV) being available in development quantities. This copolymer has been produced by fermentation of the bacterium *Ralstonia eutropha*. Fermentation and recovery processes for other PHA types have also been developed using a range of bacteria including *Azotobacter, Alcaligenes latus, Comamonas testosterone* and genetically engineered *E. coli* and *Klebsiella* and have recently been reviewed (Braunegg et al., 1998, Journal of Biotechnology 65: 127-161; Choi and Lee, 1999, Appl. Microbiol. Biotechnol. 51: 13-21). More traditional polymer synthesis approaches have also been examined, including direct condensation and ring-opening polymerization of the corresponding lactones (Jesudason and Marchessault, 1994, Macromolecules 27: 2595-2602).

Synthesis of PHA polymers containing the monomer 4-hydroxybutyrate (PHB4HB, Doi, Y. 1995, Macromol. Symp. 98, 585-599) or 4-hydroxyvalerate and 4-hydroxyhexanoate containing PHA polyesters have been described (Valentin et al., 1992, Appl. Microbiol. Biotechnol. 36, 507-514 and Valentin et al., 1994, Appl. Microbiol. Biotechnol. 40, 710-716). These polyesters have been manufactured using methods similar to that originally described for PHBV in which the microorganisms are fed a relatively expensive non-carbohydrate feedstock in order to force the incorporation of the monomer into the PHA polyester. The PHB4HB copolymers can be produced with a range of monomer compositions which again provides a range of polymer (Saito, Y, Nakamura, S., Hiramitsu, M. and Doi, Y., 1996, Polym. Int. 39: 169).

PHA copolymers containing 3-hydroxyvalerate (3HV), especially poly-3-hydroxybutyrate-co-3-hydroxyvalerate (PHBV), has been available commercially under the trade name Biopol™. PHBV has been produced commercially using *Ralstonia eutropha* (formerly *Alcaligenes eutrophus*) from carbohydrate feedstocks such as glucose in combination with a co-feed such as propionate, isobutyrate (Holmes et al., U.S. Pat. No. 4,477,654) or odd chain length alcohols or fatty acids. A number of other microorganisms and processes are known to those skilled in the art (Braunegg et al. 1998, Journal of Biotechnology 65: 127-161). PHAs containing 3HV units have also been synthesized using recombinant microorganisms. *Escherichia coli* harboring the *R. eutropha* PHA biosynthesis genes has been used to produce PHBV from glucose and either propionate or valerate (Slater et al., 1992, Appl. Environ. Microbiol. 58:1089-1094). *Klebsiella oxytoca* harboring the *R. eutropha* PHA biosynthesis genes has been used to produce PHBV from glucose and propionate (Zhang et al., 1994, Appl. Environ. Microbiol. 60:1198-1205). *R. eutropha* harboring the PHA synthase gene of *Aeromonas caviae* was used to produce poly(3HV-co-3HB-co-3HHp) from alkanoic acids of odd carbon numbers (Fukui et al., 1997, Biotechnol. Lett. 19:1093-1097). U.S. Pat. No. 6,329,183, to Skraly and Peoples, describes methods for producing PHA copolymers comprising 3HV units from 1,2-propanediol. PCT WO 00/43523 to Huisman et al., describes method for producing PHAs comprising 3-hydroxyhexanoate (3HH) monomer units from butyrate or butanol co-feeds. In each of these cases, the alcohol co-feed was converted into the free acid which was then activated to the Co-enzyme A thioester by the action of a fatty acyl-coenzymeA synthetase or fatty acyl-CoA transferase. In some cases the enzyme activity was endogenous to the host strain and in others this activity was provided by genetic engineering.

Genes and techniques for developing recombinant PHA producers suitable for practicing the disclosed invention are generally known to those skilled in the art (Madison and Huisman, 1999, Microbiology and Molecular Biology Reviews, 63: 21-53; PCT WO 99/14313).

3HV copolymers have proven useful in a range of applications. In some cases PHBV copolymers with a 3HV level of around 7-12% by weight co-monomer are adequate. In other cases a 3HV level of 15-30% by weight is more useful (EP LATEX). Higher levels of 3HV are accomplished by increasing the level of propionic acid in the feed. However, there are two negative consequences associated with this strategy. First, propionic acid is toxic to the cells and, therefore, reduces the rate of growth and polymer production representing a significant increase in the cost of production. The second effect is that some of the propionic acid can be used for other metabolic processes and is therefore not incorporated into the polymer. As the propionic acid is the most expensive of the feed components, this represents another increase in the cost of production. Therefore, it would be desirable to develop microbial systems that produce 3HV copolymers with higher productivities and better yields on the co-feed.

It is therefore an object of the present invention to provide methods and microbial strains suitable for producing PHA polymers or copolymers that avoids increasing the level of 3-hydroxyacid in the feed.

It is a further object of the present invention to provide methods and microbial strains suitable for production of PHA polymers containing 3HV units that avoids the use of 3-propionic acid in the feed.

SUMMARY OF THE INVENTION

Organisms are provided containing genes encoding one or more of Coenzyme-A-dependent aldehyde dehydrogenase, acyl-CoA transferase, acyl-CoA synthetase, β-ketothiolase, acetoacetyl-CoA reductase and PHA synthase. In some cases one or more of these genes are native to the host organism and the remainder are provided from heterologous genes through genetic engineering. These organisms produce poly (3-hydroxyalkanoate) homopolymers or co-polymers comprising 3-hydroxalkanoate monomers other than 3-hydroxybutryrate wherein these 3-hydroxyalkanoate units are derived from the enzyme-catalyzed conversion of alcohols to 3-hydroxyacyl-CoA monomers and wherein at least one step in the conversion pathway involves a Co-enzyme A-dependent aldehyde dehydrogenase activity.

The PHA polymers are readily recovered and industrially useful as polymers for articles such as films, latexes, coatings, adhesives, fibers, binders, resins and various medical devices. The medical device can be used for, for example, controlled release of therapeutic, prophylactic or diagnostic agents, tissue engineering scaffolds, cell encapsulation, targeted delivery, biocompatible coatings, biocompatible implants, guided tissue regeneration, wound dressings, orthopedic devices, prosthetics, bone cements, or diagnostics.

DETAILED DESCRIPTION OF THE INVENTION

I. Polyhydroxyalkanoate (PHA) Compositions

Figure 1:
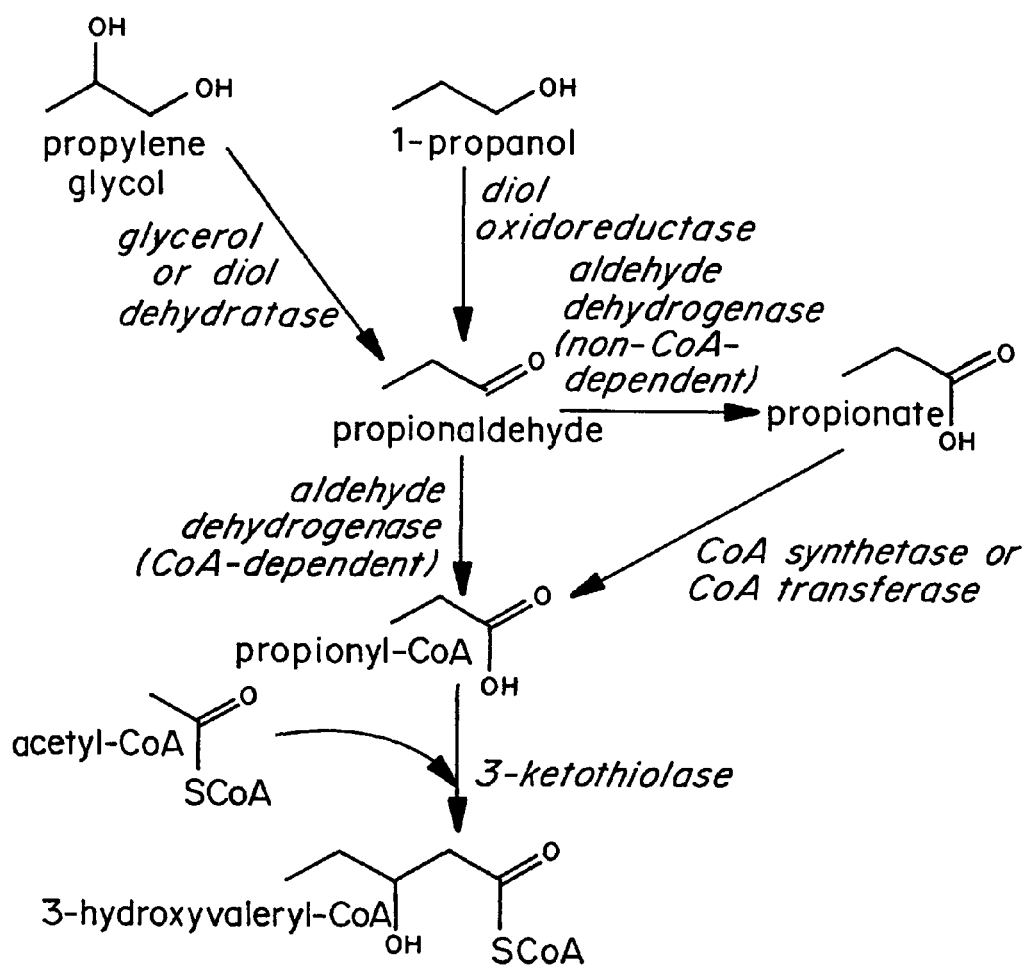
FIG. 1 shows the pathways leading to the formation of propionyl-CoA from propylene glycol and 1-propanol and butyryl-CoA from butanol.

As used herein, "PHA materials" contain one or more units, for example between 10 and 100,000, and preferably between 100 and 30,000 units of the following formula I:

$$-OCR^1R^2(CR^3R^4)_nCO-;$$

and one or more units, for example between 1 and 100,000, and preferably between 10 and 30,000 units of the following formula II:

$$-OCR^1R^2(CR^3R^4)_mCO-;$$

wherein n is an integer, for example between 1 and 15, and in a preferred embodiment, between 1 and 4;
wherein m is an integer, for example between 0 and 15, and in a preferred embodiment, between 0 and 4; and
wherein $R^1$, $R^2$, $R^3$, and $R^4$ independently can be hydrogen or hydrocarbon radicals including long chain hydrocarbon radicals; halo- and hydroxy-substituted radicals; hydroxy radicals; halogen radicals; nitrogen-substituted radicals; and/or oxygen-substituted radicals.

As used herein, the formula $-(CR^3R^4)_n-$ or $-(CR^3R^4)_m-$ is defined as including the following formulas:

$$-CR^3R^4- \text{ (where n or m=1);}$$

$$-CR^3R^4CR^{3'}R^{4'}- \text{ (where n or m=2); and}$$

$$-CR^3R^4CR^{3'}R^{4'}-CR^{3''}R^{4''}- \text{ (where n or m=3);}$$

wherein $R^3$, $R^4$, $R^{3'}$, $R^{4'}$, $R^{3''}$, and $R^{4''}$ can be independently hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms. Thus, formula I or formula II includes units derived from 3-hydroxyacids (n or m=1), 4-hydroxyacids (n or m=2), and 5-hydroxyacids (n or m=3). Formula II includes units derived from 2-hydroxyacids (m=0), for example lactic acid or glycolic acid.

The polymers typically have a molecular weight over 300, for example between 300 and $10^8$, and in a preferred embodiment 10,000 to 10,000,000 Daltons.

In a representative embodiment, the PHA polymer is a copolymer containing 3HV units. In another embodiment, the PHA polymer is a copolymer containing 3HH units.

II. Method for Biosynthesis of PHAs Containing 2-hydroxyacid Monomer (1) Synthesis of Polhydroxyalkanoate During the mid-1980's, several research groups were actively identifying and isolating the genes and gene products responsible for PHA synthesis. These efforts led to the development of transgenic systems for production of PHAs in both microorganism and plants, as well as enzymatic methods for PHA synthesis. Such routes could increase further the available PHA types. These advances have been reviewed in Williams & Peoples, $CHEMTECH,$ 26:38-44 (1996) and Williams & Peoples, $Chem.$ $Br.$ 33:29-32 (1997).

Methods which can be used for producing PHA polymers suitable for subsequent modification to alter their rates of degradation are described, for example, in U.S. Pat. No. 4,910,145 to Holmes, et al.; Byrom, "Miscellaneous Biomaterials" in $Biomaterials$ (Byrom, Ed.), pp. 333-59 (MacMillan Publishers, London 1991); Hocking & Marchessault, "Biopolyesters" in $Chemistry$ $and$ $Technology$ $of$ $Biodegradable$ $Polymers$ (Griffin, Ed.), pp.48-96 (Chapman and Hall, London 1994); Holmes, "Biologically Produced (R)-3-hydroxyalkanoate Polymers and Copolymers," in $Developments$ $in$ $Crystalline$ $Polymers$ (Bassett Ed.), vol. 2, pp. 1-65 (Elsevier, London 1988); Lafferty et al., "Microbial Production of Poly-b-hydroxybutyric acid" in $Biotechnology$ (Rehm & Reed, Eds.) vol. 66, pp. 135-76 (Verlagsgesellschaft, Weinheim 1988); Müller & Seebach, $Angew.$ $Chem.$ $Int.$ $Ed.$ $Engl.$ 32:477-502 (1993); Steinbüchel, "Polyhydroxyalkanoic Acids" in $Biomaterials$ (Byrom, Ed.), pp. 123-213 (MacMillan Publishers, London 1991); Williams & Peoples, $CHEMTECH,$ 26:38-44, (1996); Steinbüchel & Wiese, $Appl.$ $Microbiol.$ $Biotechnol.,$ 37:691-697 (1992); U.S. Pat. Nos. 5,245,023; 5,250,430; 5,480,794; 5,512,669; and 5,534,432; Agostini, et al., $Polym.$ $Sci.,$ Part A-1, 9:2775-87 (1971); Gross, et al., $Macromolecules,$ 21:2657-68 (1988); Dubois, et al., $Macromolecules,$ 26:4407-12 (1993); Le Borgne & Spassky, $Polymer,$ 30:2312-19 (1989); Tanahashi & Doi, $Macromolecules,$ 24:5732-33 (1991); Hori, et al., $Macromolecules,$ 26:4388-90 (1993); Kemnitzer, et al., $Macromolecules,$ 26:1221-29 (1993); Hori, et al., $Macromolecules,$ 26:5533-34 (1993); Hocking, et al., $Polym.$ $Bull.,$ 30:163-70 (1993); Xie, et al., $Macromolecules,$ 30:6997-98 (1997); U.S. Pat. No. 5,563,239 to Hubbs; U.S. Pat. Nos. 5,489,470 and 5,520,116 to Noda, et al. The PHAs derived from these methods may be in any form, including a latex or solid form.

Identification, cloning and expression of the genes involved in the biosynthesis of PHAs from several microorganisms within recombinant organisms allow for the production of PHAs within organisms that are not native PHA producers. A preferred example is $E.$ $coli$, which is a well recognized host for production of biopharmaceuticals, and PHAs for medical applications. Such recombinant organisms provide a greater degree of control of the PHA production process because they are free of background enzyme activities for the biosynthesis of unwanted PHA precursors or degradation of the PHA. Additionally, the proper selection of a recombinant organism facilitates purification of, or allows for increased biocompatibility of, the produced PHA.

The minimal requirements for the synthesis of PHA in a recombinant organism are a source of hydroxyalkanoyl-CoA and an appropriate PHA synthase (Gerngross & Martin, $Proc.$ $Natl.$ $Acad.$ $Sci.$ 92:6279-83(1995)). Recombinant PHA producers thus require a biosynthetic pathway for a hydroxyalkanoyl-CoA monomer and a suitable PHA synthase. Production of a homopolymer requires that the organism produce only one suitable substrate for the PHA synthase, as production of multiple substrates results in the formation of a PHA copolymer.

(2) Formation of 3-hydroxyacyl-CoA via CoA-dependent Aldehyde Dehydrogenase

Propionic acid has been the standard co-feed used for the production of 3HV-containing PHAs (Luzier, 1992, Proc. Natl. Acad. Sci. USA 89:839-842). The co-feeding strategy has the advantage that a single fermentation strain can be used to produce a PHA polymer type, usually PHBV where the 3HV concentration in the polymer can be directly controlled by modulating the level of the co-feed. Propionic acid is an anti-microbial agent, however, and therefore Increasing the level of the propionic acid co-feed results in a major increase in the fermentation time. Alternative co-feed substrates that can be used to produce 3HV-containing PHAs include threonine, odd chain fatty acids such as valerate, heptanoate, etc., and odd chain alcohols.

To become part of PHA metabolism, propionic acid must be activated by coenzyme A. Therefore an active CoA transferase or CoA synthetase must be present in the cell. In *E. coli*, this function is carried out by the ato system. The AtoDA complex is likely responsible for both uptake and CoA transfer to propionate (Jenkins and Nunn, 1987, J. Bacteriol. 169: 42-52). Thus it is useful when feeding propionate to PHBV-producing *E. coli* to use a strain which constitutively expresses atoC, the positive regulator of the ato system (Jenkins and Nunn, 1987, J. Bacteriol. 169:2096-2102). Propionyl-CoA is condensed with acetyl-CoA to give 3-hydroxyvaleryl-CoA, the activated monomer to be incorporated by the PHA synthase.

Conversion of other co-feeds such as 1-propanol or propylene glycol to propionic acid also requires a CoA synthetase or CoA transferase. Both of these co-feeds are metabolized via propionaldehyde, which may then be converted to free propionic acid.

A CoA-dependent aldehyde dehydrogenase can serve to convert propionaldehyde directly to propionyl-CoA, thus alleviating the need for a separate CoA synthetase or CoA transferase and avoiding the presence of free propionic acid in the cytosol. Propionyl-CoA is then condensed with acetyl-CoA by beta-ketothiolase to form beta-ketoacyl-CoA which is then reduced to the D-beta-hydroxyacyl-CoA by the reductase enzyme to provide the 3HV monomeric unit required for the production of copolymers containing 3HV.

The strategy is also useful for the production of other PHA copolymers. For example, a CoA-dependent aldehyde dehydrogenase can convert other aldehydes to their corresponding acyl-CoA, for example, butyraldehyde to butyryl-CoA. Following uptake into the cell, the butanol is converted to butyrate, activated to butyryl-CoA and condensed with acetyl-CoA by beta-ketothiolase to form beta-ketohexanoyl CoA which is then reduced to the D-beta-hydroxyacyl-CoA by the reductase enzyme and finally polymerized. FIG. 1 summarizes the pathways used to generate propionyl-CoA from propylene glycol and 1-propanol and butyryl-CoA from butanol.

Coenzyme A-dependent aldehyde dehydrogenase is well known. For example, Jones and Turner reported in 1984 two studies on the detection and activities of CoA-dependent aldehyde dehydrogenase (Jones and Turner, *J. Gen. Microbial* 130(Pt 2):299-308 (1984); Jones and Turner, *J. Gen. Microbiol.* 130(Pt 4):849-60 (1984)). In one embodiment, the CoA-dependent aldehyde dehydrogenase is encoded by the eutE gene of *E. coli*. Many other useful CoA-dependent aldehyde dehydrogenases are encoded by genes of other species such as described in Toth, et al., "The ald Gene, Encoding a Coenzyme A-Acylating Aldehyde Dehydrogenase, Distinguishes *Clostridium beijerinckii* and Two other Solvent-Producing Clostridia from *Clostridium acetobutylicum*" in *Applied and Environmental Microbiology* 65(11):4973-80 (1999).

Homologs of this CoA-dependent aldehyde dehydrogenase encoded by *E. coli* exist in other organisms. One can find candidate enzymes that may have the same type of activity by sequence homology which can be determined by enzyme assays. Examples of such genes are *Salmonella typhimurium* eutE (GenBank Accession No. U18560), *Listeria innocua* eutE (AL596167), *Clostridium beijerinckii* coenzyme A-acylating aldehyde dehydrogenase (AF157306), *Salmonella typhimurium* pduP (AF026270), *Vibrio cholerae* alcohol dehydrogenase/acetaldehyde dehydrogenase (AE004277), the aldehyde dehydrogenase segment of *E. coli* adhE (M33504), *Yersinia pestis* aldehyde-alcohol dehydrogenase (AJ414151), *Streptococcus pneumoniae* TIGR4 alcohol dehydrogenase, iron-containing (AE007491), *Clostridium kluyveri* CoA-dependent succinate semialdehyde dehydrogenase (L21902), and *Lactococcus lactis* alcohol-acetaldehyde dehydrogenase (AJ001008). Many other candidates can be found by using alignment techniques and databases such as GenBank at http://www.ncbi.nlm.nih.gov/blast/.

Propionaldehyde can be generated from a precursor substrate such as 1-propanol or propylene glycol and butyraldehyde can be produced from butanol. Examples of enzymes that can catalyze these conversions are diol oxidoreductase (Johnson and Lin, 1987, J. Bacteriol. 169:2050-2054; Daniel et al., 1995, J. Bacteriol. 177:2151-2156) and glycerol or diol dehydratase (Poznanskaya and Korsova, 1983, Biokhimiya 48:539-543; Tobimatsu et al., 1996, J. Biol. Chem. 271: 22352-22357) from *Klebsiella pneumoniae*, *Citrobacter freundii*, or one of several other organisms. These enzymes are found in organisms capable of converting glycerol to 1,3-propanediol, although homologs may be found in other organisms by searching databases of sequenced genes and genomes. Glycerol or diol dehydratase can convert propylene glycol to propionaldehyde in a coenzyme $B_{12}$-dependent reaction; diol oxidoreductase can convert 1-propanol to propionaldehyde in an $NAD^+$-dependent reaction.

Analogs of CoA-dependent aldehyde dehydrogenase useable in the method described herein can be identified by using alignment techniques and databases such as GenBank at http://www.ncbi.nlm.nih.gov/blast/. Generally, useable analogs have a certain degree of sequence homology, for example of 60%, 75%, 80%, 85%, 90%, 95%, 98%, or 99% or above homology, to the CoA-dependent aldehyde dehydrogenase. Sequences of known CoA-dependent aldehyde dehydrogenases in various different species are available from, for example, databases such as GenBank at http://www.ncbi.nlm.nih.gov/blast/.

Organisms provided herein contain genes encoding one or more enzymes of Coenzyme-A-dependent aldehyde dehydrogenase, acyl-CoA transferase, acyl-CoA synthetase, β-ketothiolase, acetoacetyl-CoA reductase and PHA synthase. These organisms produce poly (3-hydroxyalkanoate) homopolymers or co-polymers having 3-hydroxalkanoate monomers other than 3-hydroxybutryrate, the 3-hydroxylkanoate units being derived from the enzyme-catalyzed conversion of a chemical such as alcohols to 3-hydroxyacyl-CoA monomers and wherein at least one step in the conversion pathway involves a Co-enzyme A-dependent aldehyde dehydrogenase activity.

The organism can be a wild-type organism having a CoA-dependent aldehyde dehydrogenase activity or modified by gene mutation to have the CoA-dependent aldehyde dehydrogenase activity, or a recombinant organism in which a gene is expressed to encode the CoA-dependent aldehyde dehydrogenase. The organism can be one of bacteria, plants, yeast, and fungi. In one embodiment, the organism is bacteria such as E. coli. In another embodiment, the organism is a plant.

In one embodiment, the method described herein can be used to produce PHBV copolymers incorporating various levels of 3HV units. For example, the method provided herein can be used to produced PHA copolymers having about 30 mol % of 3HV units.

III. PHA Compositions and the Use Thereof for as Medical Devices

The polymers described herein can form various polymer compositions, which are useful for, for example, films, latexes, coatings, adhesives, fibers, binders, resins and biodegradable medical devices.

Devices prepared from the PHA copolymers described herein can be used for a wide range of different medical applications. Examples of such applications include devices for controlled release of therapeutic, prophylactic or diagnostic agents, drug delivery, tissue engineering scaffolds, cell encapsulation; targeted delivery, biocompatible coatings, biocompatible implants, guided tissue regeneration, wound dressings, orthopedic devices, prosthetics and bone cements (including adhesives and/or structural fillers), and diagnostics.

The PHA copolymers described herein can be used to encapsulate, be mixed with, or be ionically or covalently coupled to any of a variety of therapeutic, prophylactic or diagnostic agents. A wide variety of biologically active materials can be encapsulated or incorporated, either for delivery to a site by the polyhydroxyalkanoate, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Specific examples include proteins such as receptor ligands, antibodies, enzymes, blood clotting factors, inhibitors or clot dissolving agents such as streptokinase and tissue plasminogen activator; antigens for immunization; hormones and growth factors; peptides such as adhesion peptides, polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air or perfluorocarbons.

The compound is typically incorporated into the PHAs in a percent loading of between 0.1% and 70% by weight, more preferably between 5% and 50% by weight. The PHAs may be in almost any physical form, such as a powder, film, molded item, particles, spheres, latexes, and crystalline or amorphous materials. They can be combined with additional non-PHA materials, for example, other polymers. They are suitable for use in applications requiring slowly degrading, biocompatible, moldable materials, for example, medical devices. Examples of medical devices which can be prepared from the polymers include rods, bone screws, pins, surgical sutures, stents, tissue engineering devices, drug delivery devices, wound dressings, and patches such as hernial patches and pericardial patches.

Degradable implants fabricated with the PHA copolymers described herein may be used in a wide range of orthopedic and vascular applications, tissue engineering, guided tissue regeneration, and applications currently served by other thermoplastic elastomers (McMillin, *Rubber Chem. Technol.*, 67:417-46 (1994)). The implants may include other factors to stimulate repair and healing. Preferred devices are tubes suitable for passage of bodily fluids. These devices may be modified with cell attachment factors, growth factors, peptides, and antibodies and their fragments.

Preferred methods of fabricating medical devices include solvent casting, melt processing, extrusion, injection and compression molding, and spray drying. Particles are preferably prepared directly from a fermentation based process, or by a solvent evaporation technique, double emulsion technique, or by microfluidization, using methods available in the art. (Koosha, F. Ph.D. Dissertation, 1989, Univ. Nottingham, UK., *Diss. Abstr. Int. B* 51:1206 (1990); Bruhn, B. W. and Müeller, B. W. *Proceed. Intern. Symp. Control. Rel. Bioact. Mater.* 18:668-69 (1991); Conti, B. et al., *J. Microencapsulation*, 9:153-166 (1992); Ogawa, Y. et al., *Chem. Pharm. Bull.*, 36:1095-103 (1988); Mathiowitz, E. and Langer, R. "Polyanhydride microspheres as drug delivery systems," M. Donbrow Ed., in *"Microcapsules Nanopart. Med. Pharm."* CRC, Boca Raton, Fla., 1992, Ch. 5, pp. 99-123.)

The PHA copolymers described herein can be fabricated into devices for use in wound healing. For example, nonwoven fibrous materials may be prepared from the polymers by first producing polymer fibers, by pressing the polymers through a perforated outlet, using procedures known to those skilled in the art. The fibers can then be fabricated into a porous membrane (cloth) by spreading them on a solid support and subjecting them to compression molding. The thickness of the device is preferably less than 500 µm. The wound healing device may also be prepared by perforating a film or membrane using a laser to achieve porosity, or using a leaching technique to prepare a porous material. The pore sizes should ideally be small enough to lock out cells and other tissue matter. The wound healing devices may be positioned in vivo to separate tissues and stimulate tissue regeneration.

The PHA copolymers described herein may be used to encapsulate cells. Using procedures known to those skilled in the art, cells first may be pre-coated. Maysinger, *Reviews in the Neurosciences*, 6:15-33 (1995). Using a particle encapsulation procedure such as the double emulsion technique, the cells may then be encapsulated by PHAs. Ogawa, et al., *Chem. Pharm. Bull.*, 36:1095-103 (1988). Encapsulated cells may then be implanted in vivo.

The PHA polymers described herein may be fabricated into tissue engineering scaffolds using a wide range of polymer processing techniques. Preferred methods of fabricating PHA tissue engineering scaffolds include solvent casting, melt processing, fiber processing/spinning/weaving, extrusion, injection and compression molding, lamination, and solvent leaching/solvent casting. Such methods are known to those skilled in the art.

One preferred method of fabricating a PHA copolymers described herein tissue engineering scaffold involves using an extruder, such as a Brabender extruder. For example, this technique can be used to prepare extruded tubes suitable for implantation in a range of lengths and sizes.

Another preferred method involves preparing a nonwoven PHA scaffold from fibers. Fibers may be produced from the melt or solution, and processed into nonwovens using methods known to those skilled in the art. The properties of the nonwoven may be tailored by varying, for example, the PHA material, the fiber dimensions, fiber density, material thickness, fiber orientation, and method of fiber processing. The porous membranes may, if desired, be further processed. For example, these membranes may be formed into hollow tubes.

Another preferred method involves melt or solvent processing a suitable PHA into an appropriate mold and perforating the material using a laser or other means to achieve the desired porosity. Also preferred are methods that include rolling a compression molded PHA sheet into a loop and heat sealing. The PHA sheet optionally may be rolled with another material, such as a second biodegradable polymer. For example, the latter material could be a nonwoven of polyglycolic acid, polylactic acid, or a copolymer of glycolic and lactic acids. Such a procedure should provide a laminated tube suitable for use in the engineering of new vessels, ducts and tubes. The PHAs may also be used to coat other tissue engineering scaffolds. Such materials could be derived from other degradable polymers. Coating may be performed, for example, with a solvent based solution, or by melt techniques, or using a PHA latex.

The tissue engineering devices described herein may be seeded with cells prior to implantation or after implantation. The cells may be harvested from a healthy section of the donor's tissue, expanded in vitro using cell culture techniques, and then seeded into a scaffold (or matrix) either prior to or after implantation. Alternatively, the cells may be obtained from other donor's tissue or from existing cell lines.

The PHA copolymers described herein may be used to coat other devices and materials. Such coatings may improve their properties for medical application, for example, improving their biocompatibility, mechanical properties, and tailoring their degradation and controlled release profiles. The PHA copolymers described herein may be coated onto other devices using the fabrication procedures described above. The thickness of the coating can be adjusted to the needs of the specific application by changing the coating weight or concentration applied, and/or by overcoating.

The PHA copolymers described herein may be fabricated into stents using a wide range of polymer processing techniques. Preferred methods of fabricating PHA stents include solvent casting, melt processing, fiber processing/spinning, extrusion, injection molding, and compression molding. Such methods are known to those skilled in the art.

Prior to implantation, a bioresorbable polymeric article must be sterilized to prevent disease and infection of the recipient. Sterilization is performed prior to seeding a polymeric device with cells. Heat sterilization of PHA containing articles is often impractical since the heat treatment could deform the article, especially if the PHA has a melting temperature below that required for the heat sterilization treatment. This problem can be overcome using cold ethylene oxide gas as a sterilizing agent. Exposure of a PHA containing article to vapors of ethylene oxide prior to implantation sterilizes the article making it suitable for implantation. During sterilization with cold ethylene oxide gas, the PHA containing article maintains its shape. This type of treatment is ideally suited for sterilization of molded, or pre-formed articles where the shape of the article plays in important role in its proper functioning.

The devices described herein can be administered systemically or locally, or even used in vitro, particularly for cell culture. The preferred methods of systemically administering devices such as microparticles are by injection, inhalation, oral administration and implantation. Other suitable methods for administering the devices include administering the devices topically, in a lotion, ointment, patch, or dressing.

The following examples further illustrate the methods and copolymers disclosed herein.

EXAMPLE 1

Isolation and Identification of CoA-dependent Aldehyde Dehydrogenase

Because of its homology to the gene encoding the CoA-dependent aldehyde dehydrogenase component of the multifunctional alcohol dehydrogenase protein (AdhE) of *E. coli*, the eutE gene was amplified from the *E. coli* genome using the following oligonucleotide primers:

```
                                         (SEQ ID NO: 1)
5'-GGT GGT ACC TTA AGA GGA GGT TTT TAT GAA TCA ACA
GGA TAT TGA ACA-3' (eutE 5'Acc65I).

(SEQ ID NO: 2)
5'-GGT GCG GCC GCT TAA ACA ATG CGA AAC GCA TCG-
3' (eutE 3'NotI).
```

The PCR product was digested with Acc 65I and NotI and ligated to pSE380 (Invitrogen; La Jolla, Calif.) that had been cut with the same enzymes. The resulting plasmid, which contained the eutE gene under control of the IPTG-inducible trc promoter, was designated pMS35.

*E. coli* DH5α propagating either pMS35 or pTrcN (the same as pTrc99a, Pharmacia; Uppsala, Sweden except with the NotI restriction site eliminated) was grown overnight in 2 mL Luria-Bertani (LB) broth (Difco; Detroit, Mich.) plus 100 µg/mL ampicillin at 37° C. with shaking at 250 rpm. These were used as inocula for 100-mL cultures of the same medium, which were grown at 37° C. with shaking in 250-mL Erlenmeyer flasks until the optical density at 600 nm had reached 0.55 for the pTrcN-containing cells and 0.57 for the pMS35-containing cells. Then 1.3 mM IPTG was added, and the incubations were continued for 2 hours. The cells were removed from the medium by centrifugation for 10 min at 2000×g, washed once in 50 mM potassium phosphate (pH 7.0), centrifuged again, and frozen at −20° C. The cells were prepared for sonication by resuspension in a small volume of ice-cold 50 mM AMPD (pH 8.5). Sonication was carried out with a microtip for 2 minutes (0.7 seconds on, 0.3 seconds off). The crude cell extracts were obtained by spinning the sonicated cells for 10 min in an Eppendorf 5415C microcentrifuge (Brinkmann Instruments, Inc.; Westbury, N.Y.) at maximum speed at 4° C. and collecting the supernatant. The final assay mixture contained AMPD (pH 8.5, 50 mM), dithiothreitol (5 mM), NAD$^+$ (2 mM), coenzyme A (0.5 mM), 1-5 µL/mL crude cell extract, and 15 mM propionaldehyde. In a quartz cuvette, all components except for the aldehyde were combined and mixed well. After a steady absorbance reading at 340 nm was established, propionaldehyde was added and mixed by pipetting. The initial rate of change of absorbance was used to calculate the enzyme activity assuming an extinction coefficient of 6.22 mM$^{-1}$ cm$^{-1}$ for NADH. Alternatively, the assay was done with no coenzyme A. One unit of enzyme activity was defined as the amount of enzyme necessary to reduce 1 µmol of propionaldehyde per min. When CoA was included, the pTrcN extract showed no activity, but the pMS35 extract gave an activity of about 13 U/mg total protein when both 10.5 and 52.5 µg protein/mL were used. Without CoA, neither extract was active. Thus it was concluded that eutE encodes a CoA-dependent aldehyde dehydrogenase.

The same assay was done on a separate pair of extracts, generated in the same way as above, but with butyraldehyde as the substrate. The extracts were from *E. coli* DH5a once again, and this time pMS35 was compared to pMS31, which is analogous to pMS35 except that it contains the *E. coli* aldA gene. The pMS31 extract (at up to 170 μg protein/mL) showed no activity, whether or not coenzyme A was added to the assay mixture. The pMS35 extract gave an average activity of 5.9 U/mg total protein when 7.5 to 15.0 μg protein/mL were used. Without CoA, however, the pMS35 extract at the same concentrations gave an average of only about 0.1 U/mg total protein. Thus the EutE protein also acts on butyraldehyde in a CoA-dependent manner.

EXAMPLE 2

Difference in Toxicity Between Propionate and 1-propanol

*E. coli* strain MBX1335 was grown in the presence of propionate or 1-propanol to compare the inhibition of growth rate effected by these compounds. One important reason for finding alternatives to propionate feeding is that propionate slows the rate of growth and metabolism in fermentations.

Figure 2:
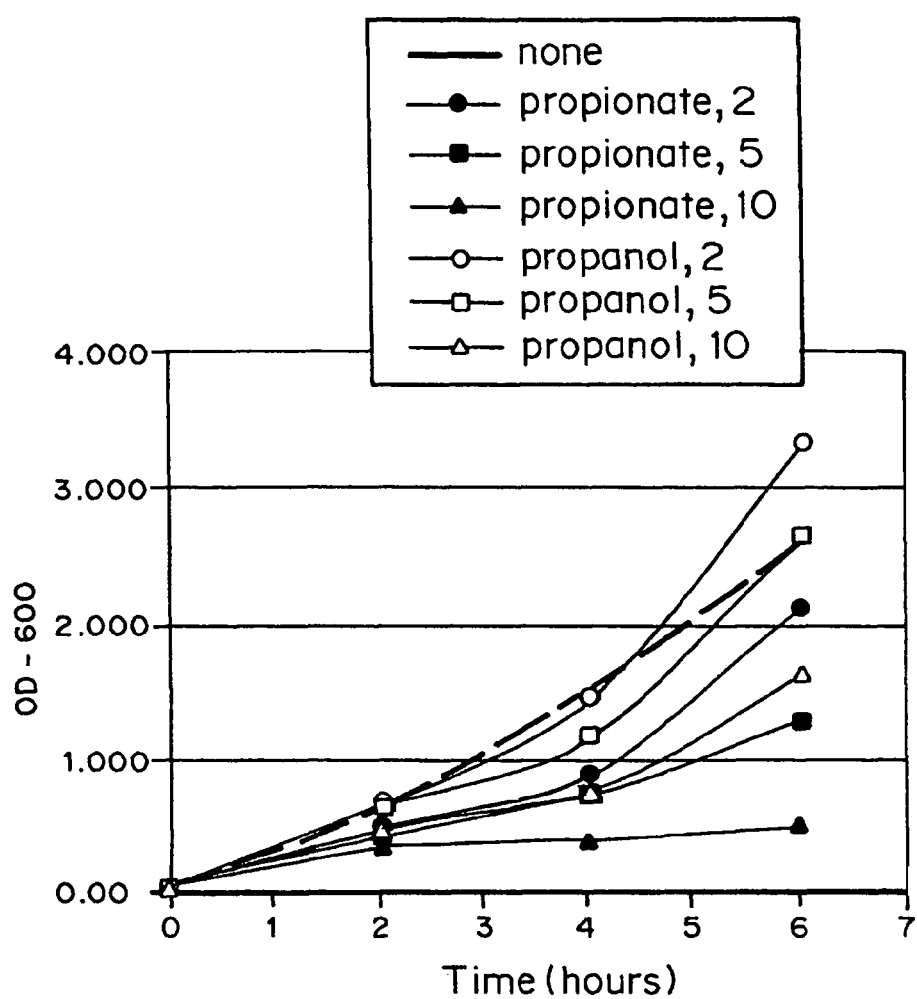
FIG. 2 shows the growth rates of $E.$ $coli$ strain MBX1335 in the presence of no inhibitor, propionate, or 1-propanol.

MBX1335 was grown overnight in LB medium supplemented with 25 μg/mL chloramphenicol. This culture was used to inoculate several 3-mL cultures of minimal medium supplemented with varying concentrations of propionate or 1-propanol. The base medium in these 3-mL cultures contained, per liter: 5 g glucose; 1 mmol $MgSO_4$; 10 mg thiamine; 25.5 mmol $Na_2HPO_4$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; 0.1 g casein hydrolysate; and 25 μg chloramphenicol. This medium also contained either sodium propionate (pH 7), 1-propanol, or no added substrate. The propionate and 1-propanol concentrations used were 2, 5, and 10 g/L. The experiment for each of these cases was done in triplicate. FIG. 2 shows the growth curves determined for each case. Clearly propionate inhibits the rate of growth substantially more than 1-propanol.

If the cultures are allowed to continue to grow, it should be noted that even though the cells grow more slowly in the presence of propionate, eventually they reach a higher optical density than in the presence of 1-propanol, presumably because they can use propionate as a carbon source for growth. The cultures with 10 g/L propionate, for example, reached an average OD-600 of 5.0, while the cultures with 10 g/L 1-propanol reached 3.8 and the cultures with no inhibitor reached 3.7. It is not desirable for the cells to grow on the co-feed because they can use the less-expensive primary feed for this purpose. Hence, 1-propanol may offer the additional advantage that it is converted more completely to PHBV and not used up by other cellular metabolism.

EXAMPLE 3

PHBV Production from Glucose and 1-propanol in Wild-type and Alcohol Dehydrogenase-deregulated Strains The *Escherichia coli* strains DC675 and DC698 are described in Clark and Rod, J. Mol. Evol. 25:151-158 (1987). Strain DC698 is a regulatory mutant which produces alcohol dehydrogenase (the product of the adhE gene) constitutively. Strain DC675, from which DC698 was derived, only produces alcohol dehydrogenase under anaerobic conditions, as is generally true for wild-type *E. coli* strains. Each of these strains was transduced with a bacteriophage P1 lysate of *E. coli* strain MBX1335, which stably expresses PHB synthesis genes from the chromosome.

A bacteriophage P1 lysate of MBX1335 was made as follows: MBX1335 was grown to an optical density (600 nm) of about 0.2 in 3 mL Luria broth (LB). Calcium chloride was added to 10 mM, and 30 μL of a P1 lysate made previously was added. The mixture was incubated at 37° C. for 4 h. After the incubation, 50 μL of chloroform was added, and the mixture was agitated vigorously. The supernatant was collected by centrifuging for 3 min in a microcentrifuge at top speed and pipetting into a screw-cap glass tube. An addition of 30 μL chloroform was made, and the resulting mixture was stored at 4° C.

Transductions were carried out on strains DC675 and DC698 as follows: each strain was grown to stationary phase in 2 mL of LB medium, and calcium chloride was added to 10 mM. In microcentrifuge tubes, 200 μL of each culture was combined with 100 μL of the P1 lysate described above or plain LB medium. These four tubes were incubated at 37° C. for 15 min, then 100 μL of 1 M sodium citrate and 500 μL LB were added to each. After a further incubation at 37° C. for 30 min, the cells were removed from the liquid by centrifuging for 10 sec in a microcentrifuge at top speed. Each pellet was resuspended in 100 μL of 100 mM sodium citrate, and the contents of each tube were plated onto selective agar medium (LB supplemented with 25 μg/mL chloramphenicol). The plates were incubated overnight at 37° C., and only the cultures treated with lysate yielded colonies. One colony was taken from each of these two plates. The DC675 transductant was denoted MBX1579, and the DC698 transductant was denoted MBX1580.

Strains MBX1579 and MBX1580 were grown overnight at 37° C. with shaking in 2 mL of a medium containing, per liter: 5 g glucose; 1 mmol $MgSO_4$; 10 mg thiamine; 25.5 mmol $Na_2HPO_4$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; and 25 μg chloramphenicol. These cultures were then added to 50 mL of the same medium as above, and 15 mL of 2×YT medium (Difco; Detroit, Mich.) was added to each for a total volume of 65 mL. These cultures were incubated at 37° C. with shaking in 250-mL Erlenmeyer flasks for 16 hours. At the conclusion of this period, the cells were removed from the medium by centrifugation for 10 min at 2000×g. They were then resuspended in 50 mL of a medium containing, per liter: 5 g glucose; 0 or 5 g 1-propanol; 7.75 g 2×YT powder; 1 mmol $MgSO_4$; 10 mg thiamine; 25.5 mmol $Na_2HPO_4O$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; and 25 μg chloramphenicol. At the conclusion of this period, the cells were removed from the medium by centrifugation as above, washed with water, centrifuged again, and lyophilized. About 15 mg of lyophilized cell mass from each flask was subjected to simultaneous extraction and butanolysis at 110° C. for 3 hours in 2 mL of a mixture containing (by volume) 90% 1-butanol and 10% concentrated hydrochloric acid, with 2 mg/mL benzoic acid added as an internal standard. The water-soluble components of the resulting mixture were removed by extraction with 3 mL water. The organic phase (1 μL at a split ratio of 1:50 at an overall flow rate of 2 mL/min) was analyzed on an SPB-1 fused silica capillary GC column (30 m; 0.32 mm ID; 0.25 μm film; Supelco; Bellefonte, Pa.) with the following temperature profile: 80° C., 2 min; 10 C° per min to 250° C.; 250° C., 2 min. The standard used was PHBV (Aldrich Chemical Co.; Milwaukee, Wis.). The polymer content and composition for each culture is given in Table 1.

TABLE 1

PHBV production in MBX1579 and MBX1580 from glucose and 1-propanol.

| Strain | 1-Propanol (g/L) | PHA, % of dry cell weight | 3HV, % of polymer weight |
|---|---|---|---|
| MBX1579 | 0 | 24.1 | 0.0 |
| MBX1580 | 0 | 42.4 | 0.0 |
| MBX1579 | 5 | 22.6 | 3.9 |
| MBX1580 | 5 | 32.7 | 24.4 |

When 1-propanol is provided, MBX1579 is capable of incorporating some 3HV units into the polymer, but MBX1580, with constitutive alcohol dehydrogenase, incorporates about six times as much, in terms of the 3HV composition by weight percentage of the polymer. MBX1579 and MBX1580 largely have the same genetic background, and thus it appeared likely that the product of the adhE gene was at least partially responsible for this increase.

EXAMPLE 4

PHBV from Glucose and 1-propanol with Plasmid-based Strain

Plasmid pMS72 contains both the *K. pneumoniae* dhaT gene and the *E. coli* eutE gene under the control of an IPTG-inducible promoter. pMS72 was constructed by inserting the eutE gene into pTC42 (Skraly et al., 1998, Appl. Environ. Microbiol. 64:98-105). The eutE gene was removed from pMS35 by digestion with BglII and SpeI. This fragment was ligated to pTC42 that had been digested with BglII and NheI (which shares a compatible sticky end with NheI).

*E. coli* strain MBX1335 was transformed with pMS72 to assess whether this construct was capable of converting glucose and 1-propanol to PHBV. MBX1335 transformed with pTrcN, the vector from which pMS72 was derived, was used as a control. Each strain was grown overnight in minimal glucose medium supplemented with 100 μg/mL ampicillin at 37° C. in a culture tube in a volume of 3 mL with shaking at 200 rpm. The minimal medium contained, per liter: 25.5 mmol $Na_2HPO_4$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; 1 mmol $MgSO_4$; 10 mg thiamine; 100 mg ampicillin; and 5 g glucose. This culture (0.1 mL) was used to inoculate a 200-mL square glass bottle containing 50 mL of the same medium. Added to each culture was 15 mL 2×YT medium (Difco; Detroit, Mich.). These 65-mL cultures were incubated with shaking at 37° C. for 6 hours with shaking at 200 rpm. At the conclusion of this period, the cells were removed from the medium by centrifugation for 10 min at 2000×g. They were then resuspended in 50 mL of the minimal glucose medium above, supplemented with 5 g/L 1-propanol; 0.5×YT; 100 μg/mL ampicillin; and 0, 0.01, or 0.05 mM IPTG. After an incubation of 90 hours at 30° C., the cells were centrifuged as above, washed once with water, centrifuged again, and lyophilized. The dried cell mass was subjected to butanolysis as described above, and the GC results are as listed in Table 2.

TABLE 2

PHBV production in MBX1335 from glucose and 1-propanol.

| Plasmid | IPTG (mM) | PHA, % of dry cell weight | 3HV, % of polymer weight |
|---|---|---|---|
| pTrcN | 0 | 19.1 | 0.0 |
| pTrcN | 0.01 | 16.1 | 3.3 |
| pTrcN | 0.05 | 18.8 | 3.5 |
| pMS72 | 0 | 14.0 | 0.0 |
| pMS72 | 0.01 | 6.6 | 9.7 |
| pMS72 | 0.05 | 6.5 | 26.3 |

Thus pMS72 enables MBX1335 to synthesize PHBV from glucose and 1-propanol much more efficiently than without the plasmid.

EXAMPLE 5

PHBV from Glucose and 1,2-propanediol with Plasmid-based Strain

*Escherichia coli* strain MBX1335 containing the plasmid pFS83 (which contains the *Klebsiella pneumoniae* glycerol dehydratase, or dhaB, gene and the *E. coli* eutE aldehyde dehydrogenase gene) was grown for 6 hours at 37° C. in LB medium in a culture tube in a volume of 3 mL with shaking at 200 rpm. This culture (0.25 mL) was used to inoculate a 250-mL Erlenmeyer flask containing 50 mL of a medium containing, per liter: 25.5 mmol $Na_2HPO_4$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; 10 g glucose; 1 mmol $MgSO_4$; 10 mg thiamine; 0.1 g casein hydrolysate; 0.01 mmol isopropyl-β-D-thiogalactopyranoside (IPTG); 100 mg ampicillin; 0 or 20 nmol coenzyme B-12; and 0, 5, or 10 g 1,2-propanediol. These 50-mL cultures were incubated with shaking at 30° C. for 24 hours with shaking at 200 rpm. At the conclusion of this period, the cells were removed from the medium by centrifugation for 10 min at 2000×g. They were washed once with water, centrifuged again, and lyophilized. The dried cell mass was subjected to butanolysis as described above, and the GC results are as listed in Table 3.

TABLE 3

PHBV production in MBX1335/pFS83 from glucose and 1,2-propanediol.

| Coenzyme B-12 (nM) | 1,2-Propanediol (g/L) | PHA, % of dry cell weight | 3HV, % of polymer weight |
|---|---|---|---|
| 0 | 0 | 58.8 | 0.0 |
| 0 | 5 | 54.8 | 0.0 |
| 0 | 10 | 54.9 | 0.0 |
| 20 | 0 | 57.6 | 0.0 |
| 20 | 5 | 49.3 | 10.9 |
| 20 | 10 | 38.3 | 16.9 |

PHBV is formed only in the presence of both coenzyme B-12 and 1,2-propanediol, strongly suggesting that the action of the coenzyme B-12-dependent glycerol dehydratase is responsible for the conversion of 1,2-propanediol to propionaldehyde, which is ultimately incorporated into the polymer as 3HV.

The plasmid pFS83 was constructed by taking the eutE gene from pMS35 as an XbaI-HindIII fragment and ligating this fragment to pFS44B cut with SpeI and HindIII. Plasmid pFS44B was constructed by ligating the SalI-NheI fragment of pTC53 (Skraly et al., 1998, Appl. Environ. Microbiol.

64:98-105) containing the dhaB gene to the vector pSE380 (Invitrogen; Carlsbad, Calif.) that had been digested with the same restriction enzymes.

EXAMPLE 6

PHBV from Glucose and 1-propanol with Integrated Strain

Several *Escherichia coli* strains were constructed by integration of the *K. pneumoniae* dhaT and *E. coli* eutE genes, along with the tetA gene from Tn10, into the chromosome of MBX1335. The integration was accomplished with the plasmid pUT-eutE-dhaT-tetA, a derivative of pUTHg (Herrero et al., 1990, J. Bacteriol. 172:6557-6567). To construct pUT-eutE-dhaT-tetA, first the tetA gene was amplified by PCR from Tn10 using the following oligonucleotide primers:

(SEQ ID NO: 4)
5'-GGT CCT AGG TTA AGA GGA GGT TTT TAT GAA TAG TTC GAC AAA GAT CGC-3'(tetA 5'AvrII)

(SEQ ID NO: 5)
5'-GGT ACT AGT CTA AGC ACT TGT CTC CTG TTT AC-3'(tetA 3'SpeI).

The tetA PCR product was digested with AvrII and SpeI and ligated to pUTHg that had been digested with AvrII (AvrII and SpeI give compatible sticky ends). This resulted in plasmid pUT-tetA. The eutE and dhaT genes were taken from pMS72 by digestion with SalI and Spe I and ligated to pUC18Sfi (Herrero et al., ibid.) which had been digested with SalI and XbaI. This resulted in plasmid pMS77. Then the eutE-dhaT fragment was taken from pMS77 by digestion with AvrII, and it was ligated to pUT-tetA that had been digested with AvrII, to form pUT-eutE-dhaT-tetA. After conjugation, the donor-recipient mixture was immediately grown in LB supplemented with 15 µg/mL tetracycline and 25 µg/mL chloramphenicol for about 40 generations by serial culturing at 37° C. This enriched population was plated onto LB agar supplemented with the same antibiotics.

Several colonies were isolated from platings such as this and were tested for their ability to synthesize PHBV from glucose and 1-propanol. MBX1335 (from which it was derived) was used as a control. Each strain was grown for 8 hours in LB medium supplemented with 25 µg/mL chloramphenicol, 50 µg/mL kanamycin, and 10 µg/mL tetracycline at 37° C. in a culture tube in a volume of 3 mL with shaking at 200 rpm. This culture (1 mL) was used to inoculate a 500-mL Erlenmeyer flask containing 100 mL of a medium containing, per liter: 25.5 mmol $Na_2HPO_4$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; 10 g glucose; 5 mmol $MgSO_4$; 10 mg thiamine; 0.1 g casein hydrolysate; 25 mg chloramphenicol; 50 mg kanamycin; 10 mg tetracycline; and 7 g/L 1-propanol. These 100-mL cultures were incubated with shaking at 30° C. for 46 hours with shaking at 200 rpm. At the conclusion of this period, the cells were removed from the medium by centrifugation for 10 min at 2000×g. They were washed once with water, centrifuged again, and lyophilized. The dried cell mass was subjected to butanolysis as described above, and the GC results are as listed in Table 4. In a separate experiment, the activities of the eutE and dhaT gene products were measured. The cells were grown as above, except with 4 g/L 1-propanol instead of 7 g/L 1-propanol, and the incubation at 30° C. was for 24 h instead of 46 h. Strain LS5218 was cultured to establish a background in 100 mL LB for 8 hours at 37° C. After the incubations, 50 mL of each culture was centrifuged as above, then washed once in 25 mL of a buffer containing 50 mM HEPES (pH 7.4), 2 mM dithiothreitol, and 0.1 mM $MnCl_2$, centrifuged again, and resuspended in 2 mL of the same buffer. The suspensions were sonicated with a microtip for 2 min (0.4 sec on, 0.4 sec off), and enzyme assays conducted as in Johnson and Lin, 1987, J. Bacteriol. 169:2050-4 for DhaT and as in Yan and Chen, 1990, Appl. Environ. Microbiol. 56: 2591-9 for EutE. Results are given in Table 4.

TABLE 4

PHBV production in integrants from glucose and 1-propanol.

| Strain | Final OD-600 | Total PHA, % of dry cell wt. | 3HV, % of polymer weight | EutE activity, U/mg | DhaT activity, U/mg |
|---|---|---|---|---|---|
| LS5218 | — | — | — | 0.03 | 0.00 |
| MBX1635 | 11.8 | 57 | 4.6 | 0.21 | 0.09 |
| MBX1865 | 11.1 | 68 | 12.6 | 0.33 | 0.41 |
| MBX1866 | 11.3 | 68 | 5.9 | 0.27 | 0.12 |
| MBX1914 | 10.8 | 64 | 9.7 | 0.30 | 0.39 |
| MBX1915 | 10.5 | 63 | 10.6 | 0.24 | 0.41 |
| MBX1916 | 10.7 | 73 | 11.4 | 0.39 | 0.30 |
| MBX1917 | 9.3 | 64 | 7.6 | 0.31 | 0.26 |

Different integrated strains had differing abilities to incorporate 3HV into the polymer when fed 1-propanol, and these abilities roughly corresponded to activities of EutE and DhaT, the two enzymes responsible for conversion of 1-propanol to propionyl-CoA.

EXAMPLE 7

PHBV from Glucose and 1,2-propanediol with Integrated Strain

*Escherichia coli* strain MBX1648 was constructed by integration of the *K. pneumoniae* dhaB and *E. coli* eutE genes, along with the tetA gene from Tn10, into the chromosome of MBX1335. The integration was accomplished with the plasmid pUT-dhaB-eutE-tetA, a derivative of pUTHg (Herrero et al., 1990, J. Bacteriol. 172: 6557-6567). To construct pUT-dhaB-eutE-tetA, first the tetA gene was amplified by PCR from Tn10 as in the previous example. The tetA PCR product was digested with AvrII and SpeI and ligated to pUTHg that had been digested with AvrII (AvrII and SpeI give compatible sticky ends). This resulted in plasmid pUT-tetA. The dhaB and eutE genes were taken from pMS82 (pFS83 which was digested with AvrII, filled in by T4 DNA polymerase, and self-ligated, to remove the AvrII site) by digestion with SalI and SpeI and ligated to pUC18Sfi (Herrero et al., ibid.) which had been digested with SalI and XbaI (which shares a compatible sticky end with SpeI). This resulted in plasmid pMS83. Then the eutE-dhaB fragment was taken from pMS83 by digestion with AvrII, and it was ligated to pUT-tetA that had been digested with AvrII, to form pUT-dhaB-eutE-tetA. After conjugation, the donor-recipient mixture was immediately grown in LB supplemented with 15 µg/mL tetracycline and 25 µg/mL chloramphenicol for about 40 generations by serial culturing at 37° C. This enriched population was plated onto LB agar supplemented with the same antibiotics. MBX1648 was one colony isolated from this plating.

MBX1648 was tested for its ability to synthesize PHBV from glucose and 1,2-propanediol. MBX1335 (from which it was derived) was used as a control. Each strain was grown for 8 hours in LB medium supplemented with 25 µg/mL chloramphenicol at 37° C. in a culture tube in a volume of 3 mL with shaking at 200 rpm. This culture (0.1 mL) was used to inoculate a 250-mL Erlenmeyer flask containing 50 mL of a medium containing, per liter: 25.5 mmol $Na_2HPO_4$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; 10 g glucose; 1 mmol $MgSO_4$; 10 mg thiamine; 0.1 g casein hydrolysate; 25 mg chloramphenicol; and varying amounts of coenzyme B-12 and 1,2-propanediol, as indicated in Table 5. These 50-mL cultures were incubated with shaking at 30° C. for 46 hours with shaking at 200 rpm. At the conclusion of this period, the cells were removed from the medium by centrifugation for 10 min at 2000×g. They were washed once with water, centrifuged again, and lyophilized. The dried cell mass was subjected to butanolysis as described above, and the GC results are as listed in Table 5.

TABLE 5

PHBV production in MBX1335/pFS83 from glucose and 1,2-propanediol.

| Strain | Coenzyme B-12 (nM) | 1,2-Propanediol (g/L) | PHA, % of dry cell weight | 3HV, % of polymer weight |
|---|---|---|---|---|
| MBX1335 | 20 | 10 | 38.3 | 0.0 |
| MBX1648 | 0 | 10 | 25.0 | 0.0 |
| MBX1648 | 5 | 10 | 28.2 | 8.0 |
| MBX1648* | 10 | 10 | 2.0 | 39.0 |
| MBX1648* | 20 | 10 | 9.9 | 44.5 |
| MBX1648 | 10 | 0 | 27.8 | 0.0 |
| MBX1648 | 10 | 5 | 14.8 | 29.9 |
| MBX1648* | 10 | 20 | 27.2 | 23.8 |

*These cultures were fed 25.5 mM $Na_2HPO_4$, 33.3 mM $K_2HPO_4$, and 27.2 mM $KH_2PO_4$ at 16 h to alleviate acidity.

Thus MBX1648 can synthesize copolymers with significant 3HV content while maintaining overall polymer content under various conditions.

Those skilled in the art will recognize, or be able to ascertain using no more than routine experimentation, many equivalents to the specific embodiments of the methods and compositions described herein. Such equivalents are intended to be encompassed by the following claims.

I claim:

1. A recombinant organism selected from the group consisting of bacteria, yeast, fungi and plants for producing polyhydroxyalkanoates, comprising a heterologous gene encoding a CoA-dependent aldehyde dehydrogenase and a PHA synthase.

2. The recombinant organism of claim 1 further comprising a heterologous gene encoding a PHA synthase.

3. The recombinant organism of claim 2 further comprising one or more genes, wherein the genes encode enzymes selected from the group consisting of acyl-CoA transferase, acyl-CoA synthetase, β-ketothiolase, acetoacetyl-CoA reductase.

4. The recombinant organism of claim 3, wherein one or more of the genes are endogenous to the recombinant organism.

5. The recombinant organism of claim 3, wherein one or more of the genes encoding enzymes selected from the group consisting of acyl-CoA transferase, acyl-CoA synthetase, β-ketothiolase, acetoacetyl-CoA reductase are heterologous to the recombinant organism.

6. The recombinant organism of claim 1 wherein the gene is eutE of *E. coli*.

7. The recombinant organism of claim 1 which is a bacteria.

8. The recombinant organism of claim 1 which is a plant.

* * * * *